United States Patent
Schuhmann et al.

(10) Patent No.: US 8,951,404 B2
(45) Date of Patent: Feb. 10, 2015

(54) ELECTROCHEMICAL SYSTEM FOR MEASURING A BIOLOGICAL COMPOUND BY AN ENZYME

(75) Inventors: Wolfgang Schuhmann, Bochum (DE); Sabine Borgmann, Fagettewille, AR (US)

(73) Assignee: The Swatch Group Research and Development Ltd, Marin (CH)

( * ) Notice: Subject to any disclaimer, the term of this patent is extended or adjusted under 35 U.S.C. 154(b) by 956 days.

(21) Appl. No.: 12/375,163

(22) PCT Filed: Jul. 10, 2007

(86) PCT No.: PCT/EP2007/057012
§ 371 (c)(1),
(2), (4) Date: Jan. 26, 2009

(87) PCT Pub. No.: WO2008/012197
PCT Pub. Date: Jan. 31, 2008

(65) Prior Publication Data
US 2010/0018866 A1    Jan. 28, 2010

(30) Foreign Application Priority Data

Jul. 25, 2006    (EP) .................................. 06117822

(51) Int. Cl.
*G01F 1/64*    (2006.01)
*G01N 27/26*    (2006.01)
(Continued)

(52) U.S. Cl.
CPC ................ *C12Q 1/006* (2013.01); *C12Q 1/004* (2013.01)
USPC .................... 205/792; 205/777.5; 204/403.01

(58) Field of Classification Search
USPC ....................... 205/775, 777.5, 792; 204/403.01–403.15
See application file for complete search history.

(56) References Cited

U.S. PATENT DOCUMENTS

| 5,393,903 | A | 2/1995 | Graetzel et al. |
| 2002/0053523 | A1 | 5/2002 | Liamos et al. |
| 2007/0000776 | A1* | 1/2007 | Karube et al. ........... 204/403.01 |

FOREIGN PATENT DOCUMENTS

| JP | 05-256812 | 10/1993 |
| JP | 6-174679 A | 6/1994 |

(Continued)

OTHER PUBLICATIONS

C. Lau, S. Reiter, W. Schuhmann and P. Grundler, Application of heated electrodes operating in a non-isothermal mode for interference elimination with amperometric biosensors, Anal. Bioanal. Chem. (2004) 379: 255-260.*

(Continued)

*Primary Examiner* — Luan Van
*Assistant Examiner* — Maris R Kessel
(74) *Attorney, Agent, or Firm* — Griffin & Szipl, P.C.

(57) ABSTRACT

The system includes an electronic measuring apparatus for receiving an electrochemical sensor including a substrate that carries the current collectors for connecting the measuring and reference electrodes to the measuring apparatus. The measuring electrode is coated with a reagent including at least the specific enzyme of the biological compound to be analysed in a body fluid. The measuring apparatus can impose at least two different temperatures to enable the signal from the compound to be analysed from those of other biological compounds interfering with the signal. Application to measuring glucose in the blood with glucose dehydrogenase as the enzyme, without interference with maltose.

9 Claims, 7 Drawing Sheets

(51) Int. Cl.
*C12Q 1/00* (2006.01)
*G01N 33/50* (2006.01)

(56) References Cited

FOREIGN PATENT DOCUMENTS

| | | |
|---|---|---|
| JP | 2000-019146 | 1/2000 |
| WO | 99/46585 | 9/1999 |
| WO | WO 2005010519 A1 * | 2/2005 |

OTHER PUBLICATIONS

International Search Report issued in corresponding application No. PCT/EP2007/057012, completed Oct. 1, 2007 and mailed Oct. 10, 2007.
Lau, et al., "Improved specificity of reagentless amperometric PQQ-sGDH glucose biosensors by using indirectly heated electrodes." Biosensors and Bioelectronics 22 (2007) 3014-3020.

* cited by examiner

ELECTROCHEMICAL SYSTEM FOR MEASURING A BIOLOGICAL COMPOUND BY AN ENZYME

This is a National Phase Application in the United States of International Patent Application No. PCT/EP2007/057012 filed Jul. 10, 2007, which claims priority on European Patent Application No. 06117822.4, filed Jul. 25, 2006. The entire disclosures of the above patent applications are hereby incorporated by reference.

FIELD OF THE INVENTION

The present invention concerns an electrochemical system for measuring the level of a determined biological compound in a body fluid sample, using a specific enzyme of said biological compound, but which can interfere with other biological compounds. The invention will be more specifically illustrated by the amperometric measurement of glucose in the blood by means of glucose dehydrogenase.

BACKGROUND OF THE INVENTION

Precise monitoring of the blood glucose level is a vital precaution for a large number of patients suffering from diabetes, since these patients may also be obliged to undergo other treatments for other health problems at the same time.

Numerous miniaturized apparatus already exist for measuring the glucose level, which determines the quantity of insulin to be administered, and to make the everyday life of such patients easier. These apparatus generally rely upon an electrochemical measurement by amperometrics, in the presence of a specific enzyme in glucose, with the blood sample being deposited on a disposable sensor.

The enzyme that is currently most used is glucose oxydase (GOD) because it is very specific to glucose, to the exclusion of all other oligosaccharides, and because it is insensitive to temperature variations as regards the signal height. Glucose oxydase has, however, the drawback of being very sensitive to the presence of oxygen, whose concentration may be variable, which distorts the precise glucose level measurement. In order to reduce or eliminate this drawback, it has been proposed to use a mediator, which will accelerate the electron transfer and make the influence of oxygen negligible. From among the most used mediators, we may cite ferrocene and its derivatives, and osmium complexes, such as those disclosed in U.S. Pat. No. 5,393,903.

One could also use glucose dehydrogenase (GDH), which has the advantage of being insensitive to the presence of oxygen. Glucose dehydrogenase has, however, the drawback of being less glucose specific and of interfering with other saccharides, oligosaccharides, and oligopolysaccharides, such as maltose, which results in the glucose level being overestimated and thus to insulin being inappropriately administered. This constitutes a serious drawback for diabetic patients, who must also, for example, undergo continuous ambulatory peritoneal dialysis (CAPD) by absorbing icodextrine, which is hydrolysed by α-amylase with oligosaccharides such as maltose, maltotriose or maltotetraose.

SUMMARY OF THE INVENTION

It is thus an object of the present invention to provide a reliable electrochemical system for measuring a determined biological compound in a body fluid using of a specific enzyme of said compound, in accordance with a protocol that can differentiate the signal of the biological compound to be measured from the signal of other biological compounds. This differentiation basically relies upon the sensitivity of the biological compound to be measured and the interfering biological compounds as a function of temperature, which results in different kinetics allowing the signals of each biological compound to be separated.

The invention will be more specifically illustrated by a system for measuring the glucose level in a blood sample by electrochemical measurements using glucose dehydrogenase.

The system thus includes an electronic measuring apparatus that can receive an electrochemical sensor and impose at least two determined temperatures on the measuring electrode so that the signal belonging to the biological compound to be measured can be differentiated from the signal from another biological compound. The sensor is formed in a known manner by a substrate, carrying current collectors for connecting the measuring apparatus to at least one measuring electrode and a reference electrode of the sensor.

The reagent deposited on the measuring electrode includes at least the enzyme, but may also incorporate a cofactor of the enzyme and a mediator, such as a ferrocene derivative or an osmium complex, facilitating the electron transfer between the enzyme and the measuring electrode.

According to a first embodiment, the means for bringing the measuring electrode to at least two different temperatures are formed by a heating coil, embedded in the sensor substrate and arranged under the measuring electrode, while being electrically insulated therefrom. The coil is connected to the measuring apparatus, which will send, for example, a pulsed current, which, in accordance with prior calibration, can impose at least two determined temperatures. This enables the signal belonging to the biological compound being measured to be differentiated, by mathematical processing of the signals received at said temperatures, from the signal of another biological compound.

According to a second embodiment, the coil is integrated in the measuring apparatus, such that, when the sensor is introduced, the measuring zone is positioned above said coil.

In order to obtain at least two different temperatures at the measuring electrode, those skilled in the art can, without departing from the scope of the present invention, devise another device for bringing said measuring electrode to two different temperatures, for example via the thermostatted confinement of said electrode.

BRIEF DESCRIPTION OF THE DRAWINGS

Other features and advantages of the present invention will appear in the following description, given by way of non-limiting illustration, for measuring glucose in the blood by using glucose dehydrogenase as the enzyme, with reference to the annexed drawings, in which.

DETAILED DESCRIPTION OF A PREFERRED EMBODIMENT OF THE INVENTION

Figure 1:
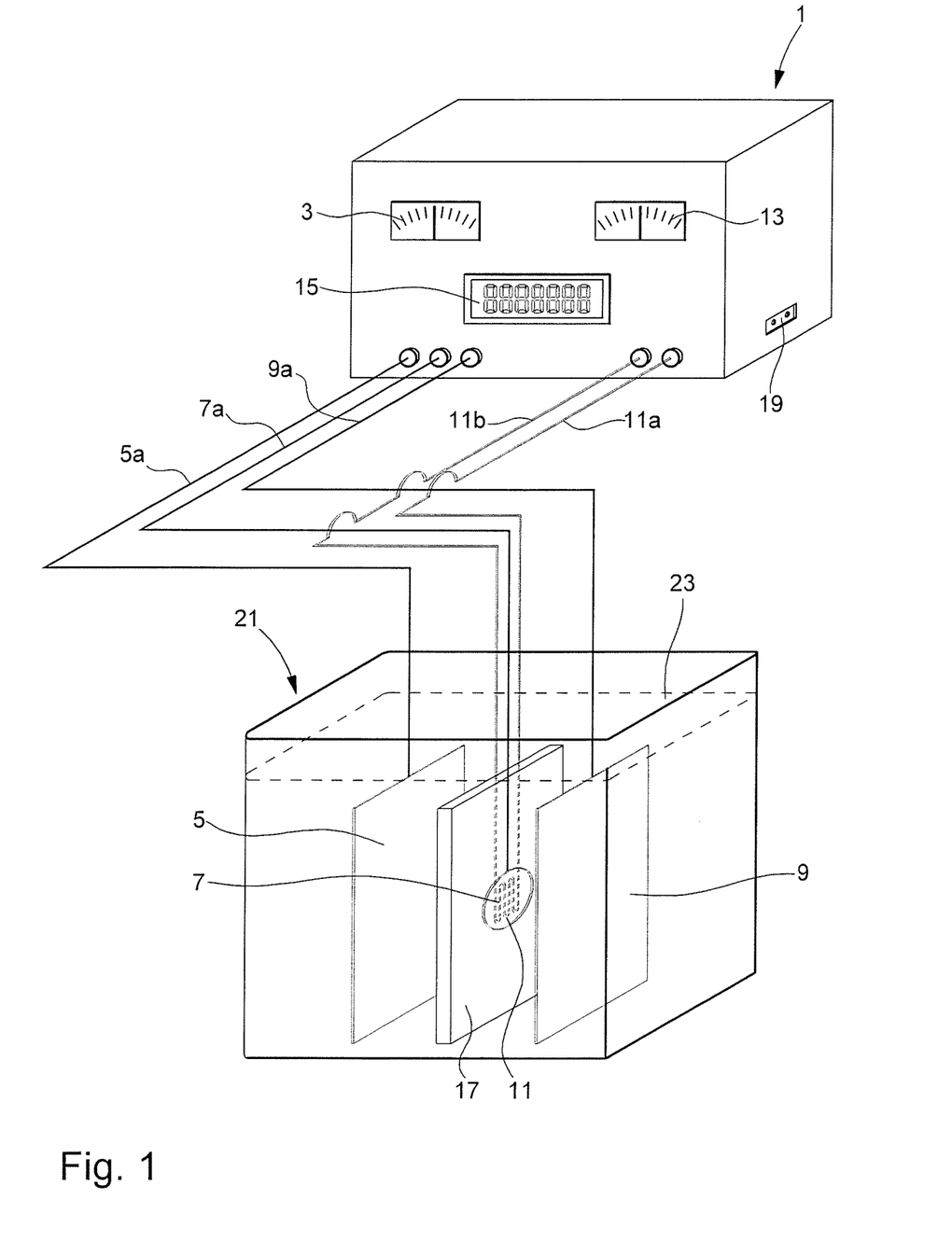
FIG. 1 is a schematic diagram of the laboratory material used within the scope of the present invention.

FIG. 1 shows schematically the laboratory material that was used for making the measurements and experiments explained below. The system includes an electronic control case 1, which has a potentiostat 3, connected to the reference electrode 5 made of Ag/AgCl/3M KCl, to measuring electrode 7 and to counter-electrode 9, both of which are made of platinum, respectively by connectors 5a, 7a and 9a. The control case 1 includes a second potentiostat 13, whose connection cables 11a, 11b can impose a pulsed or non-pulsed current on a heating coil 11 embedded in a ceramic substrate 17 carrying measuring electrode 7, formed by a platinum disc that is 2 mm in diameter, formed by screen-printing at the surface of said substrate 17.

The design of heating device 11 enables the temperature at the surface of measuring electrode 7 to be varied without noticeably influencing the temperature of the medium, preferably without influencing the mass temperature of the sample drop to be tested, which is arranged on the electrodes. The mass therefore preferably remains at ambient temperature. The heating of the place where the electrochemical reactions occur between the sample and the electrodes will thus preferably be localised and rapid.

Potentiostat 13, in conjunction with an associated control member, can impose several different temperatures, typically two to eight temperatures, in accordance with the features of a pulsed current, as will be explained below. The apparatus further includes a visual display 15 of the measurement carried out and/or connecting means 19 for an electronic apparatus (not shown), which, for example, displays the result of the measurement being made in the form of a graph, compared to prior measurements.

The system also includes a vat 21, shown in larger scale and including an electrolyte 23, able to receive measuring or test samples. The electrolyte has the following composition in all of the measurements carried out: 20 mM HEPES, 20 mM KCl and 1 mM $CaCl_2$.

It should be noted that, according to a variant, vat 21 can be omitted and in such case the sample is formed by a drop directly placed on the measuring electrodes as described below.

In this example, measuring electrode 7 is covered with a reagent including PQQ-sGDH (glucose dehydrogenase with pyrroloquinoline as cofactor) and an osmium complex acting as mediator to facilitate the electron transfer between the enzyme and the electrode.

The reagent is preferably deposited in the form of an anodic electrodeposition hydrogel (EDP), in accordance with a known technique. Any other method of deposition may also be suitable, for example the deposition could be achieved simply by pipetting.

Figure 2:
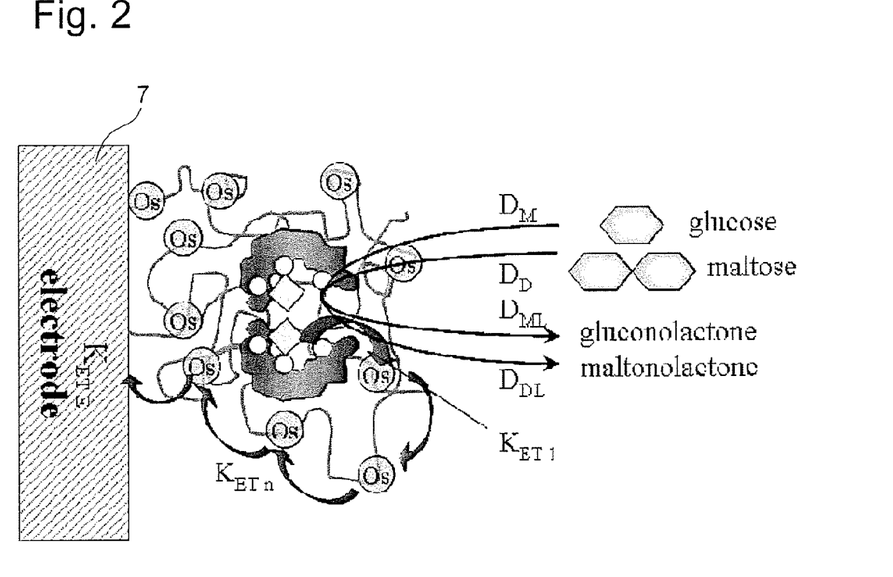
FIG. 2 is a simplified diagram of the reactions at the measuring electrode.

FIG. 2 is a simplified diagram of reactions at the surface of the measuring electrode when the medium to be analyzed contains both glucose and maltose, which is a glucose dimmer. In this diagram, $D_M$ represents the glucose diffusion coefficient, $D_D$ the maltose diffusion coefficient, $D_{ML}$ the gluconolactone diffusion coefficient, and $D_{DL}$ the maltolactone diffusion coefficient. $K_{ET\,1}$ is the electron transfer coefficient between the pyrroloquinoline quinone (PQQ) in the active site of the enzyme and the osmium complex of the polymer structure, $K_{ET\,n}$ is the electron jump coefficient in the osmium polymer and $K_{ET\,E}$ represents the electrochemical oxidation of $Os^{++}$ into $Os^{+++}$ at the surface of measuring electrode 7.

Those skilled in the art could, of course, envisage using different enzymes from glucose dehydrogenase with other cofactors and other mediators to obtain the current representative of the desired chemical reactions, one of which is illustrated in FIG. 2. Typically, mediators could be chosen from among osmium, ruthenium or ferrocene compounds.

Figure 3:
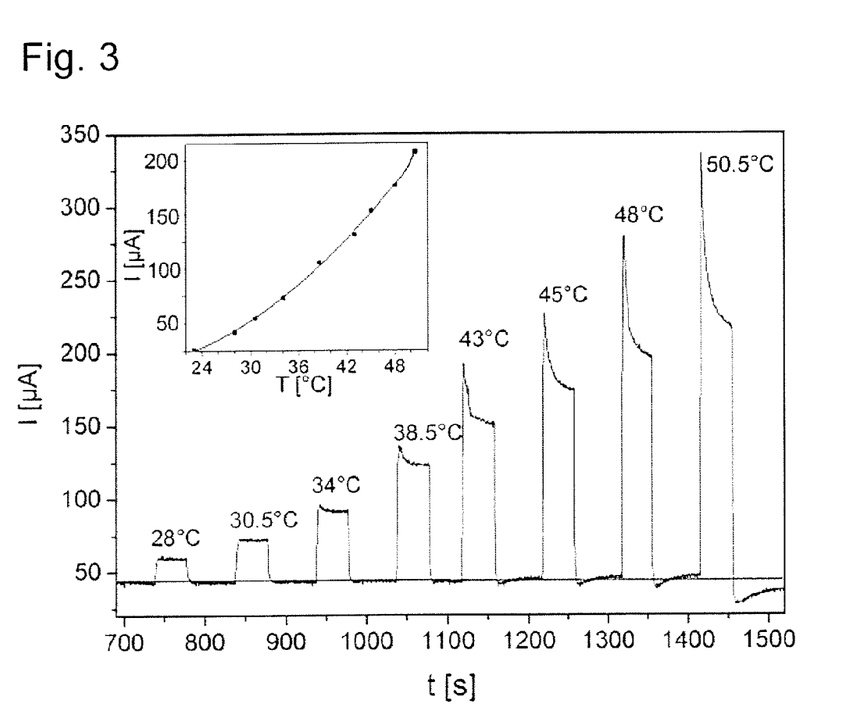
FIG. 3 is a temperature calibration diagram for the sensor.

FIG. 3 is a temperature calibration diagram, i.e. a diagram that gives the temperature at the surface of the measuring electrode of the sensor as a function of a determined current applied for a known time period. The known potentiometric calibration method is used for this, by applying a determined voltage in pulsed mode to the heating coil by means of a DC/AC or similar converter.

The electrochemical measurements are carried out by amperometry by imposing a voltage comprised between 0 and 750 mV, and preferably 300 mV, between the electrodes, depending upon the construction features of the sensor.

The example of FIG. 3 shows the result of these measurements when 8 impulses, each lasting 40 seconds, are applied, determining increasing temperatures measured at the surface of the measuring electrode, while the current of the sensor, which is dipped into a buffer medium containing 0.15 mM glucose, is continuously amperometrically recorded. As can be seen, this enables the temperature to vary between 28° C. and 50.5° C. As shown in the inserted diagram, an applied intensity can be correlated with a given temperature. The description below will be limited to a temperature of less than 50° C., since it has been observed that beyond this value there is a drop in activity by the PQQ cofactors. In practice, in the following experiments, a current pulsed at 7 impulses of 30 seconds each is used, for imposing 7 different temperatures represented in the graphs of FIGS. 4 to 7 by the symbols in brackets: 23° C. (□) corresponding to the ambient temperature, 28° C. (0), 30° C. (Δ) 34° C. (+), 38° C. (◊), 43° C. (star), 48° C. (*).

Figure 4:
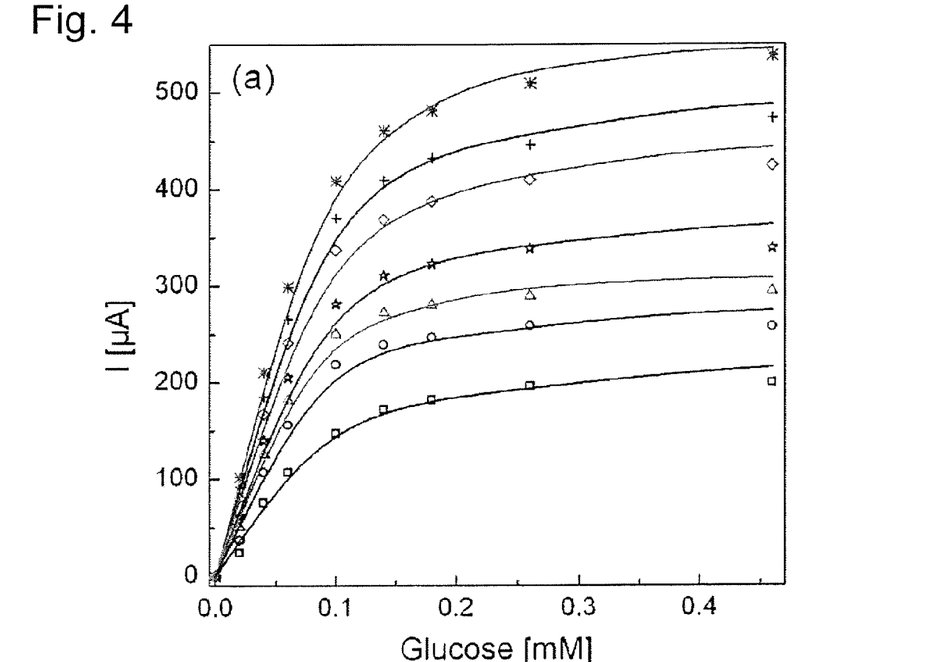
FIGS. 4 and 5 show the responses of the sensor at different temperatures, as a function, respectively, of glucose or maltose concentrations.
Figure 5:
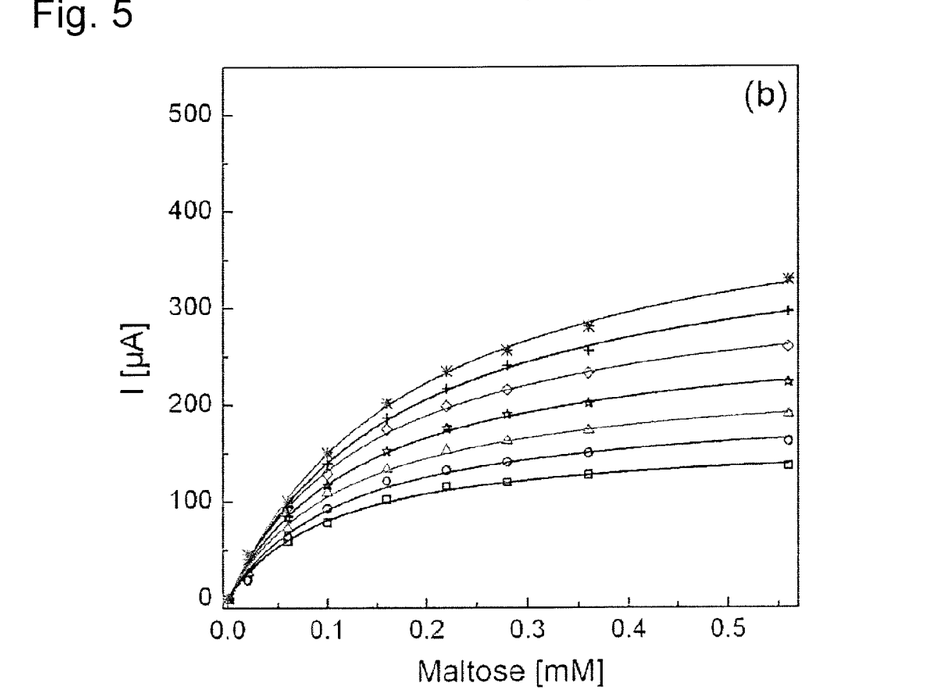

FIGS. 4 and 5 show, in the form of a graph, respectively for glucose and for maltose, groups of curves showing the response of the sensor for increasing concentrations of the compound to be analysed at the aforementioned different temperatures. As can be seen, in the same concentration, the sensor response current is significantly higher for glucose than for maltose.

Figure 6:
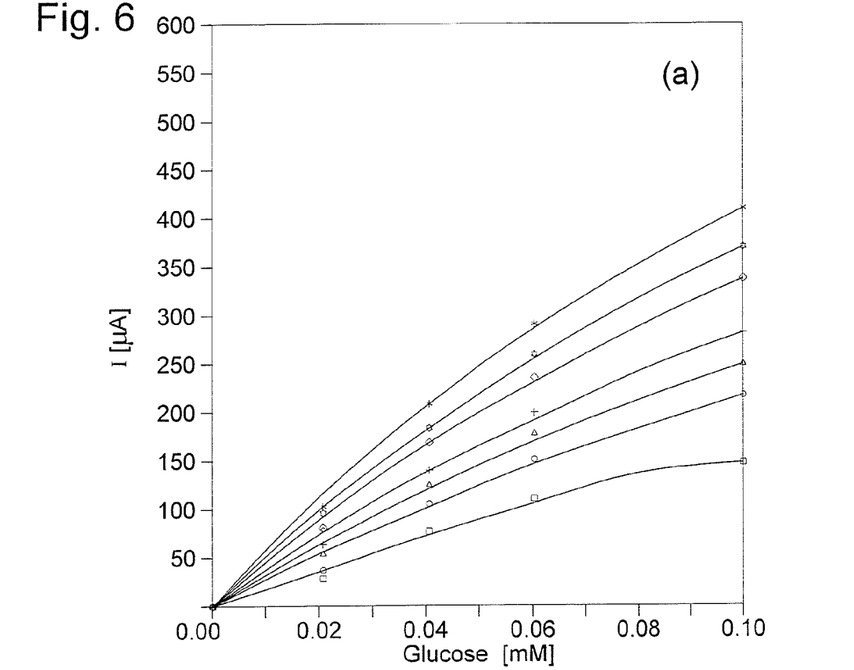
FIGS. 6 and 7 show the responses of the sensor at different temperatures as a function of different concentrations of glucose, respectively without and with maltose.
Figure 7:
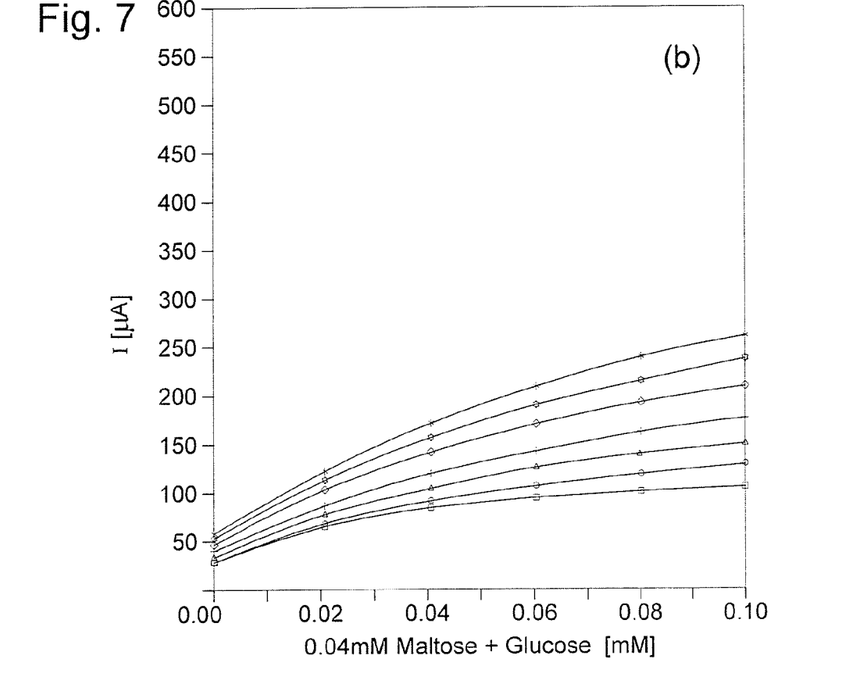

Referring now to FIGS. 6 and 7, the preceding experiment is repeated with increasing concentrations of glucose alone (FIG. 6), then in the presence of 0.04 mM of maltose (FIG. 7). As can be seen, the sensor response is lower in the presence of maltose, which can be explained by competitive inhibition of glucose oxidation because the active site of the enzyme is blocked by the maltose.

Owing to this automated heating protocol and to perfectly localised temperature variations in only one narrow zone at the surface of the sensor, which hardly alters the electrolyte temperature at all, a large number of measurements have been obtained for different concentrations of compounds to be analysed at different temperatures.

Figure 8:
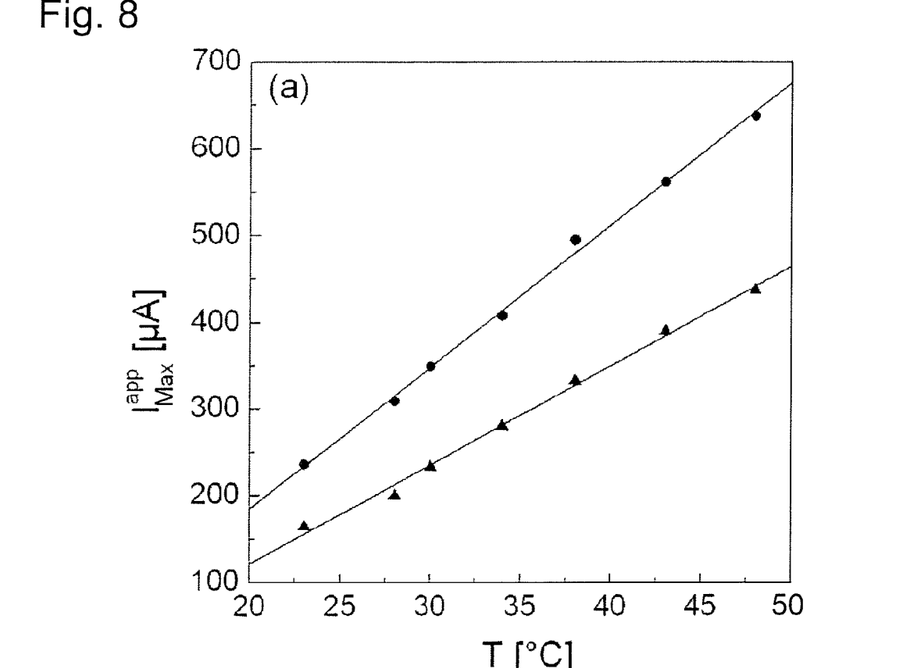
FIGS. 8 and 9 show, as a function of temperature, the sensor response for glucose and maltose, respectively as regards the apparent maximum intensity and the apparent Michaelis constant.
Figure 9:
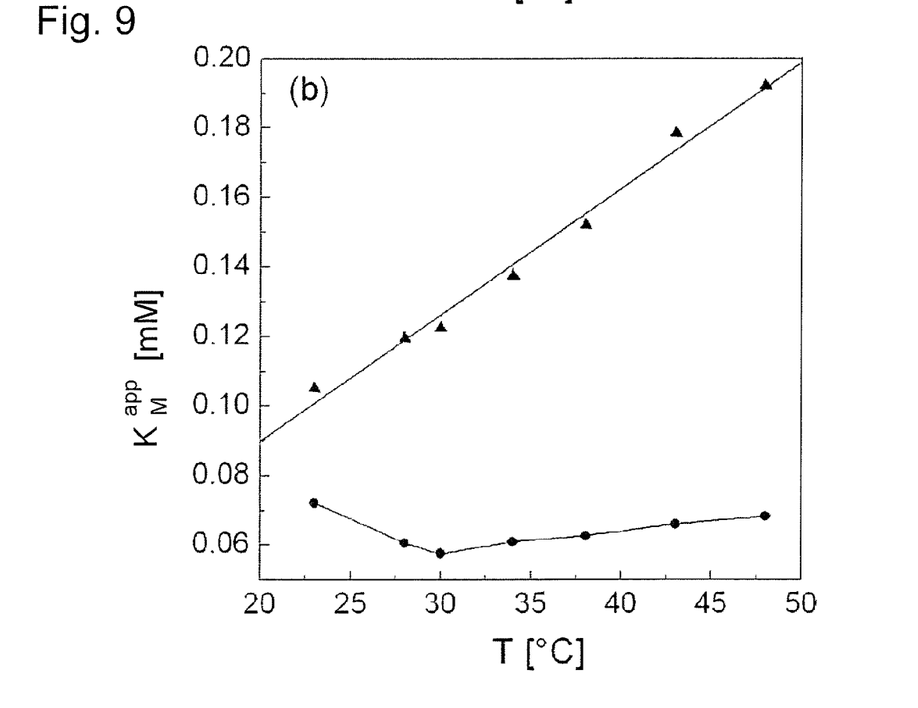

As shown in FIGS. 8 and 9, the performance of the sensor has now been evaluated by means of the apparent maximum current $I_{Max}^{app}$ (FIG. 8) and the apparent Michaelis constant, $K_M^{app}$ (FIG. 9), both for glucose (●), and for maltose (▲). An almost linear increase in $I_{Max}^{app}$ can be observed in FIG. 8 for both compounds, measured as a function of the temperature increase, with the glucose signal, however, being slightly higher.

Conversely, FIG. 9 clearly shows at $K_M^{app}$, significantly different behavior by glucose and maltose as a function of temperature increase. As can be seen, the glucose value of $K_M^{app}$ is practically unaffected by the temperature increase. Conversely, the maltose value of $K_M^{app}$ very clearly shows an almost linear increase as a function of temperature, which enables the glucose signal to be differentiated from the maltose signal.

Given the differences in variation in $K_M^{app}$ for glucose and for maltose as a function of temperature, i.e. as a function of their different kinetics, it is possible to differentiate the signals and separate them by mathematical processing via multiple linear regression, using the current intensity at different temperatures as the input value and the glucose concentration as the output value.

Figure 10:
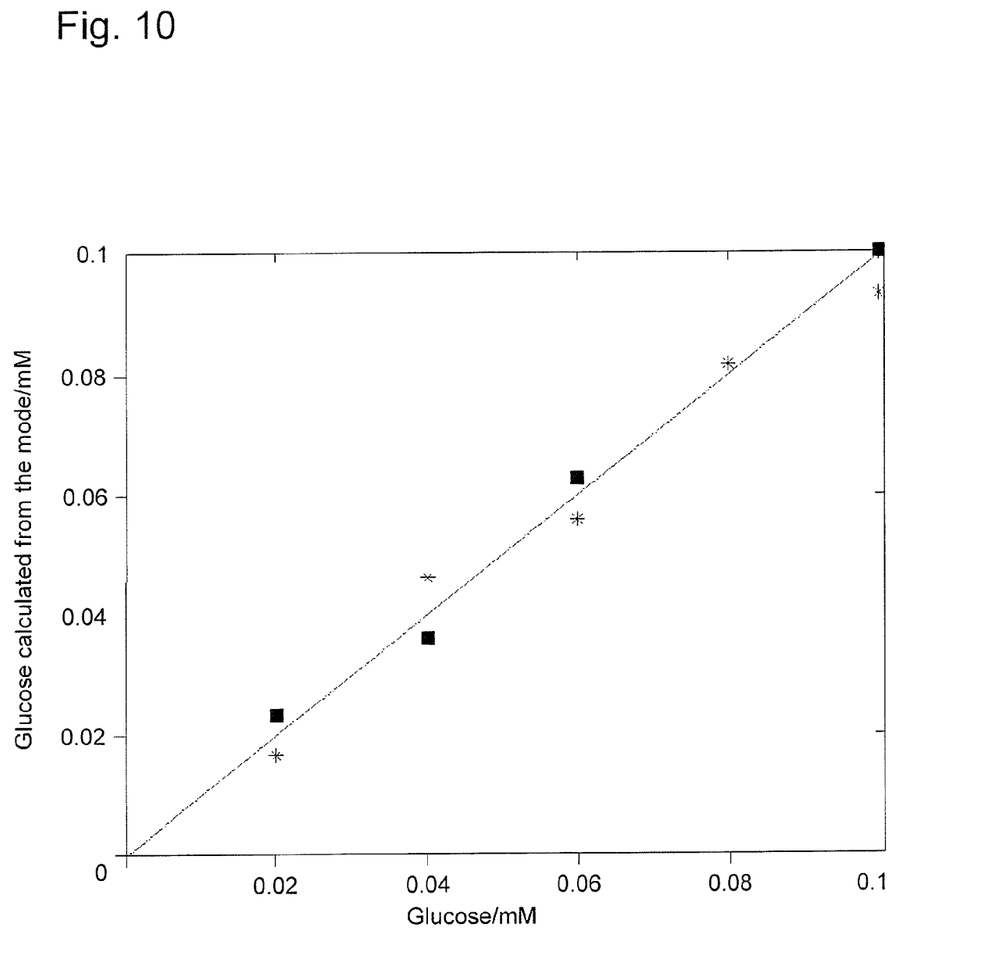
FIG. 10 is a graph showing the correlation between the measurements taken and the theory, for measuring glucose without maltose and in the presence of maltose.

Experiments have been carried out on the results obtained with a glucose/maltose mixture having glucose concentrations of 0; 0.02; 0.04; 0.06; 0.08 and 0.1 mM and a maltose concentration of respectively 0 mM (■) and 0.04 mM (*). The graph of FIG. 10 shows, on the abscissa, the measured glucose level, and on the y axis, the calculated glucose level. As can be seen, there is a high level of precision in the determination of the glucose level, whether or not maltose is present. The high performance level of the model proposed in accordance with the invention is confirmed both by the high value of the determination coefficient $R^2=0.968$, and by the low values of the mean quadratic error value RMSE=0.0018 mM and the mean relative error MRE=8.8%.

Referring now to FIGS. 11 to 14, a portable device is shown, in accordance with various embodiments, which has all of the functions of the system described in FIG. 1, but whose miniaturization enables the diabetic patient to have the device with him wherever he goes.

Figures 11, 12, 13, 14:
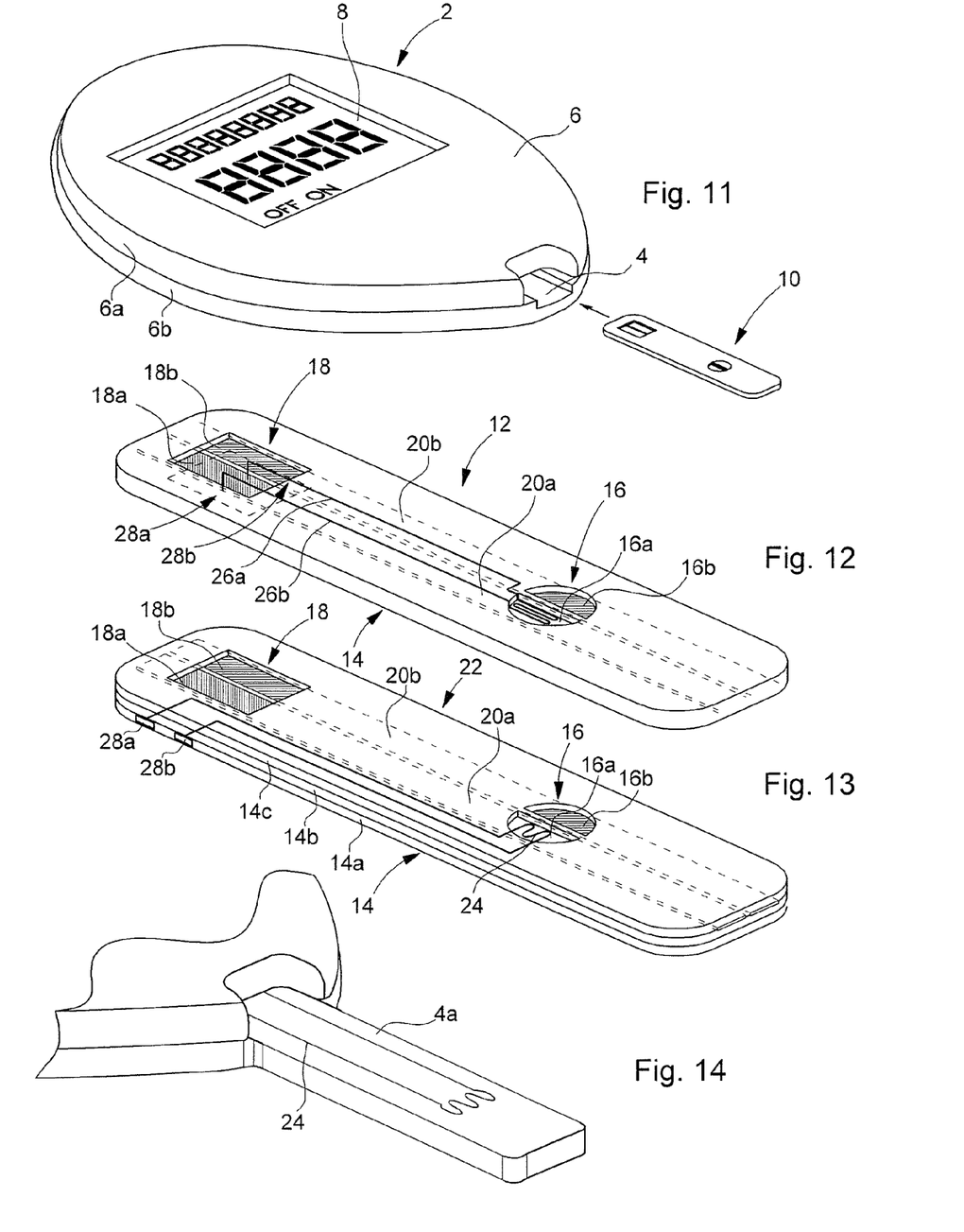
FIG. 11 shows a portable device according to the invention for measuring a glucose level.
FIG. 12 is an enlarged diagram of a sensor according to a first embodiment.
FIG. 13 is an enlarged diagram of a sensor according to a second embodiment.
FIG. 14 is an enlarged diagram of one part of the measuring apparatus, according to yet another embodiment.

The device includes a measuring apparatus 2 for receiving an electrochemical sensor 10 in a slot 4 made in its case 6, formed of two shells 6a, 6b. Case 6 includes a display screen 8 for displaying the result of a measurement. The case contains a power source or is connected to a power source, and an electronic circuit (not shown) for both imposing a determined voltage between the electrodes of sensor 10 and powering a heating circuit of the measuring electrode, as will be understood more clearly with reference to FIG. 12. FIG. 12 shows, on a larger scale, a sensor 12 according to a first embodiment of the invention.

In this first embodiment, sensor 12 is made from a substrate 14 for example, made of multi-layered sintered ceramic material, or similar materials, and includes, in a known manner, a measuring aperture 16 revealing the measuring electrode 16a and the reference electrode 16b and a connecting aperture 18, revealing connecting zones 18a, 18b. The electrodes 16a, 16b and the connecting zones 18a, 18b are connected by conductive paths 20a, 20b embedded in the ceramic material. For example, the measuring electrode is coated with a reagent having the aforementioned composition, namely a reagent containing at least PQQ-sGDH and an osmium complex, applied across said electrode by anodic electrodeposition of a hydrogel (EDP) or suchlike.

The sensor further includes a heating coil 24 made of platinum and arranged underneath measuring electrode 16a while embedded in the ceramic material. Coil 24 is connected by conductors 26a, 26b to contact zones 28a, 28b, which, in this example are located underneath connecting zones 18a, 18b. Obviously, the heating circuit is totally electrically insulated from the circuit powering the electrodes. Sensor 12, which has just been described, only has two electrodes, but it is clear that it could also include a counter-electrode.

FIG. 13 shows a second embodiment, which essentially differs from the preceding embodiment in that substrate 14 is made of plastic. In the example shown, substrate 14 is obtained by stacking three substrates 14a, 14b, 14c in the form of PET tongues, which can easily withstand a temperature not exceeding 50° C. Bottom substrate 14a carries heating coil 24 and conductors 26a, 26b as far as contact zones 28a, 28b, which, in this example, are arranged on one edge of the sensor. The top face of intermediate substrate 14b carries the electrodes 16a, 16b, conductive paths 20a, 20b and connecting zones 18a, 18b, which are thus perfectly electrically insulated from the heating coil 24. The top substrate includes measuring aperture 16 and connecting aperture 18.

In both of the embodiments that have just been described, heating coil 24 is integrated in the sensor itself. According to a variant shown in FIG. 14, coil 14 is separated from the sensor by being arranged in a plate 4a that extends slot 4 of measuring apparatus 2, such that measuring electrode 16a is positioned underneath said coil 24 when the sensor is engaged in slot 4. In these conditions, the sensor can have an entirely conventional shape, designated by the reference 10 in FIG. 11, when the glucose level is measured using glucose oxydase.

Without departing from the scope of the invention, those skilled in the art can make certain alterations to the examples that have just been described, for example, by thinning the insulating portion of the substrate located between the measuring electrode and the heating coil, or by using another device for imposing at least two different temperatures on the measuring electrode.

The invention claimed is:

1. A method for measuring a glucose level in a blood sample by electrochemical measurements using a glucose enzyme that can interfere with other biological compounds, including the steps of:
   (a) depositing the blood sample in a measuring zone of an electrochemical sensor including a reference electrode and a measuring electrode coated with a reagent including at least the glucose enzyme;
   (b) introducing the sensor into a measuring apparatus of a device, wherein the sensor includes the reference electrode, the measuring electrode, and a heating means that heats the measuring electrode, wherein the measuring apparatus is connected to an electrical power source and further includes an electronic circuit that imposes a variable or non-variable current, or a variable or non-variable voltage, between the electrodes and the heating means;
   (c) heating the measuring electrode, via the heating means, to at least two different temperatures during one measuring run, thereby obtaining a signal for each temperature; and (d) submitting the signal for each temperature obtained from the measuring electrode to a device for differentiating a signal indicative of the glucose from at least one other signal indicative of at least one other biological compound by monitoring the behavior of the apparent Michaelis constant of signals obtained as a function connected of temperature increase.

2. The method according to claim 1, wherein the device comprises a programmed device for processing signal via multiple linear regression.

3. The method according to claim 1, wherein the glucose enzyme is glucose dehydrogenase.

4. The method according to claim 3, wherein the reagent includes pyrroloquinoline as a cofactor of glucose dehydrogenase.

5. The method according to claim 4, wherein the reagent further includes an a mediator that facilitates an electron transfer between the glucose enzyme and the measuring electrode that is selected from the group consisting of osmium, ruthenium and ferrocene compounds.

6. The method according to claim 1, wherein the device is portable.

7. The method according to claim 1, wherein the method further comprises the step of:
   (e) differentiating a signal belonging to glucose from an interference signal belonging to other saccharides, oligasaccharides or oligapolysaccharides.

8. A method for measuring a glucose level in a blood sample by electrochemical measurements using a glucose enzyme that can interfere with other biological compounds, the method comprising the steps of:
   (a) depositing a blood sample in a measuring zone of an electrochemical sensor including a reference electrode and a measuring electrode coated with a reagent including at least the glucose enzyme;
   (b) wherein the sensor includes the reference electrode and the measuring electrode, wherein the measuring apparatus includes a heating means that heats the measuring electrode of the sensor, wherein the measuring apparatus is connected to an electrical power source and further includes an electronic circuit that imposes a variable or non variable intensity, or a variable or non variable voltage, between the electrodes and the heating means;
   (c) heating the measuring electrode, via the heating means, to at least two different temperatures during one measuring thereby obtaining a signal for each temperature; and
   (d) submitting the signals obtained for each temperature from the measuring electrode, to a device for differentiating a signal indicative of the determined compound from at least one other signal indicative of at least one other biological compound by monitoring the behavior of the apparent Michaelis constant of signals obtained as a function of temperature increase.

9. The method according to claim 8, wherein the method further comprises the step of:
   (e) differentiating a signal belonging to glucose from an interference signal belonging to other saccharides, oligasaccharides or oligapolysaccharides.

* * * * *